United States Patent
Cazzini et al.

(10) Patent No.: US 8,460,355 B2
(45) Date of Patent: *Jun. 11, 2013

(54) NEGATIVE/POSITIVE PRESSURE, THERMAL ENERGY THERAPY DEVICE

(75) Inventors: Karl H. Cazzini, Orchard Park, NY (US); Thomas P. Stewart, Orchard Park, NY (US)

(73) Assignee: Stryker Corporation, Kalamazoo, MI (US)

( * ) Notice: Subject to any disclaimer, the term of this patent is extended or adjusted under 35 U.S.C. 154(b) by 1422 days.

This patent is subject to a terminal disclaimer.

(21) Appl. No.: 11/784,057

(22) Filed: Apr. 5, 2007

(65) Prior Publication Data

US 2008/0249593 A1   Oct. 9, 2008

(51) Int. Cl.
*A61F 7/00* (2006.01)
*A61H 7/00* (2006.01)

(52) U.S. Cl.
USPC .............. 607/111; 607/104; 607/108; 601/6; 601/9; 601/151; 601/152

(58) Field of Classification Search
USPC .................. 607/96, 104, 108, 111; 601/6, 9, 601/152

See application file for complete search history.

(56) References Cited

U.S. PATENT DOCUMENTS

| | | |
|---|---|---|
| 1,202,605 A | 10/1916 | Storm, Jr. |
| 2,113,253 A | 4/1938 | Gray |
| 2,832,336 A | 4/1958 | Davis et al. |
| 3,186,404 A | 6/1965 | Gardner |
| 3,450,450 A | 6/1969 | Hopkins et al. |
| 3,516,411 A | 6/1970 | Adler |
| 3,785,374 A | 1/1974 | Lipson |
| 3,859,989 A | 1/1975 | Spielberg |
| 4,139,004 A | 2/1979 | Gonzalez, Jr. |
| 4,421,109 A | 12/1983 | Thornton |
| 4,428,368 A | 1/1984 | Torii |
| 4,772,259 A | 9/1988 | Frech et al. |
| 4,966,135 A | 10/1990 | Renfrew |
| 5,000,164 A | 3/1991 | Cooper |
| 5,074,285 A | 12/1991 | Wright |
| 5,080,089 A | 1/1992 | Mason et al. |
| 5,107,832 A * | 4/1992 | Guibert et al. ............. 607/96 |
| 5,109,832 A | 5/1992 | Proctor et al. |
| 5,117,812 A | 6/1992 | McWhorter |
| 5,245,990 A | 9/1993 | Bertinin |
| 5,358,467 A | 10/1994 | Milstein et al. |
| 5,417,720 A | 5/1995 | Mason |
| 5,489,259 A | 2/1996 | Jacobs et al. |

(Continued)

OTHER PUBLICATIONS

General Electric's Jan. 1966 definition of vacuum-tight seal, found at http://stinet.dtic.mil/oai/oai?&verb=getRecord&metadataPrefix=html&identifier=ADA075554.

(Continued)

*Primary Examiner* — Linda Dvorak
*Assistant Examiner* — Kaitlyn Smith
(74) *Attorney, Agent, or Firm* — Warner Norcross & Judd LLP

(57) ABSTRACT

A negative/positive pressure, thermal energy therapy device is described in this application. The present invention uses a conventional negative pressure, thermal energy device and/or an alternative embodiment thereof and adds a significant modification. The modification is that positive pressure, not just ambient pressure, is at least occasionally applied to the patient's body contained in the negative pressure, thermal energy device.

12 Claims, 2 Drawing Sheets

U.S. PATENT DOCUMENTS

| | | | |
|---|---|---|---|
| 5,554,103 | A | 9/1996 | Zheng et al. |
| 5,674,262 | A | 10/1997 | Tumey |
| 5,683,438 | A | 11/1997 | Grahn |
| 5,688,225 | A | 11/1997 | Walker |
| 5,868,690 | A | 2/1999 | Eischen, Sr. |
| 5,997,540 | A | 12/1999 | Zheng et al. |
| 6,135,116 | A | 10/2000 | Vogel et al. |
| 6,149,674 | A | 11/2000 | Borders |
| 6,488,643 | B1 | 12/2002 | Tumey et al. |
| 6,565,593 | B2 | 5/2003 | Diana |
| 6,589,194 | B1 | 7/2003 | Calderon et al. |
| 6,602,277 | B2 | 8/2003 | Grahn et al. |
| 6,656,208 | B2 | 12/2003 | Grahn et al. |
| 6,673,099 | B2 | 1/2004 | Grahn et al. |
| 6,689,079 | B2 | 2/2004 | Flick et al. |
| 6,916,289 | B2 | 7/2005 | Schnall |
| 6,945,944 | B2 | 9/2005 | Kuiper et al. |
| 6,966,922 | B2 | 11/2005 | Grahn et al. |
| 6,974,442 | B2 | 12/2005 | Grahn et al. |
| 7,122,047 | B2 | 10/2006 | Grahn et al. |
| 7,182,776 | B2 | 2/2007 | Grahn et al. |
| 7,306,568 | B2 | 12/2007 | Diana |
| 7,520,889 | B2 | 4/2009 | Van Duren |
| 7,540,848 | B2 | 6/2009 | Hannigan et al. |
| 7,591,795 | B2 | 9/2009 | Whalen et al. |
| 8,052,624 | B2 * | 11/2011 | Buchanan et al. ............. 601/11 |
| 8,226,586 | B2 | 7/2012 | Cazzini et al. |
| 2002/0019657 | A1 | 2/2002 | Elkins |
| 2003/0097163 | A1 * | 5/2003 | Kane et al. ................. 607/108 |
| 2003/0125649 | A1 | 7/2003 | McIntosh et al. |
| 2003/0216672 | A1 | 11/2003 | Rastegar et al. |
| 2004/0010212 | A1 | 1/2004 | Kuiper et al. |
| 2004/0068310 | A1 | 4/2004 | Edelman |
| 2004/0082886 | A1 | 4/2004 | Timpson |
| 2004/0133135 | A1 | 7/2004 | Diana |
| 2005/0027218 | A1 * | 2/2005 | Filtvedt et al. ............... 601/152 |
| 2005/0033390 | A1 | 2/2005 | McConnell |
| 2005/0126578 | A1 | 6/2005 | Garrison et al. |
| 2005/0143797 | A1 | 6/2005 | Parish et al. |
| 2005/0203452 | A1 | 9/2005 | Weston et al. |
| 2005/0251117 | A1 | 11/2005 | Anderson et al. |
| 2005/0261615 | A1 | 11/2005 | Weston |
| 2006/0100556 | A1 | 5/2006 | Hargens et al. |
| 2006/0111766 | A1 | 5/2006 | Grahn et al. |
| 2006/0122670 | A1 | 6/2006 | Grahn et al. |
| 2006/0211958 | A1 * | 9/2006 | Rosenberg et al. ............. 601/9 |
| 2006/0235346 | A1 | 10/2006 | Prescott |
| 2006/0235497 | A1 | 10/2006 | Zanotti |
| 2006/0287621 | A1 | 12/2006 | Atkinson et al. |
| 2007/0055188 | A1 | 3/2007 | Avni et al. |
| 2007/0060987 | A1 | 3/2007 | Grahn et al. |
| 2007/0093730 | A1 | 4/2007 | Chan et al. |
| 2007/0123962 | A1 | 5/2007 | Grahn et al. |
| 2007/0167884 | A1 | 7/2007 | Mangrum et al. |
| 2008/0021531 | A1 | 1/2008 | Kane et al. |
| 2008/0064992 | A1 | 3/2008 | Stewart et al. |
| 2008/0077202 | A1 | 3/2008 | Levinson |
| 2008/0077205 | A1 | 3/2008 | Cazzini |
| 2008/0082029 | A1 | 4/2008 | Diana |
| 2008/0132816 | A1 | 6/2008 | Kane et al. |
| 2008/0132976 | A1 * | 6/2008 | Kane et al. ................... 607/104 |
| 2008/0208088 | A1 | 8/2008 | Cazzini et al. |
| 2009/0012434 | A1 * | 1/2009 | Anderson ...................... 601/6 |
| 2009/0014004 | A1 | 1/2009 | Whalen et al. |
| 2009/0036959 | A1 | 2/2009 | Filtvedt et al. |
| 2009/0048649 | A1 | 2/2009 | Peret et al. |
| 2009/0120433 | A1 | 5/2009 | Loori et al. |
| 2009/0194115 | A1 | 8/2009 | Squitieri |
| 2009/0259169 | A1 | 10/2009 | Loori et al. |
| 2009/0299239 | A1 | 12/2009 | Meyer et al. |
| 2009/0312675 | A1 | 12/2009 | Sampson et al. |
| 2010/0010408 | A1 | 1/2010 | Linares |
| 2010/0095641 | A1 | 4/2010 | Ruetenik |
| 2010/0106230 | A1 * | 4/2010 | Buchanan et al. ............. 607/111 |
| 2010/0121230 | A1 | 5/2010 | Vogel et al. |
| 2010/0152633 | A1 * | 6/2010 | Rein et al. ................... 601/152 |
| 2010/0152821 | A1 * | 6/2010 | Rein et al. ................... 607/96 |
| 2011/0288458 | A1 * | 11/2011 | Jones et al. ................... 601/149 |

OTHER PUBLICATIONS

Office Action dated Jul. 13, 2011 for commonly-assigned copending U.S. Appl. No. 11/709,587.
Office Action dated Feb. 2, 2010 for commonly-assigned copending U.S. Appl. No. 11/709,587.
Office Action dated Jul. 9, 2009 for commonly-assigned copending U.S. Appl. No. 11/709,587.
Office Action dated Dec. 26, 2008 for commonly-assigned copending U.S. Appl. No. 11/709,587.
Office Action dated Jun. 11, 2008 for commonly-assigned copending U.S. Appl. No. 11/709,587.
Office Action dated Jul. 13, 2011 for U.S. Appl. No. 11/709,587.
Apr. 24, 2012 Office Action for commonly assigned copending U.S. Appl. No. 11/893,446, which corresponds to 2009/0048649.

* cited by examiner

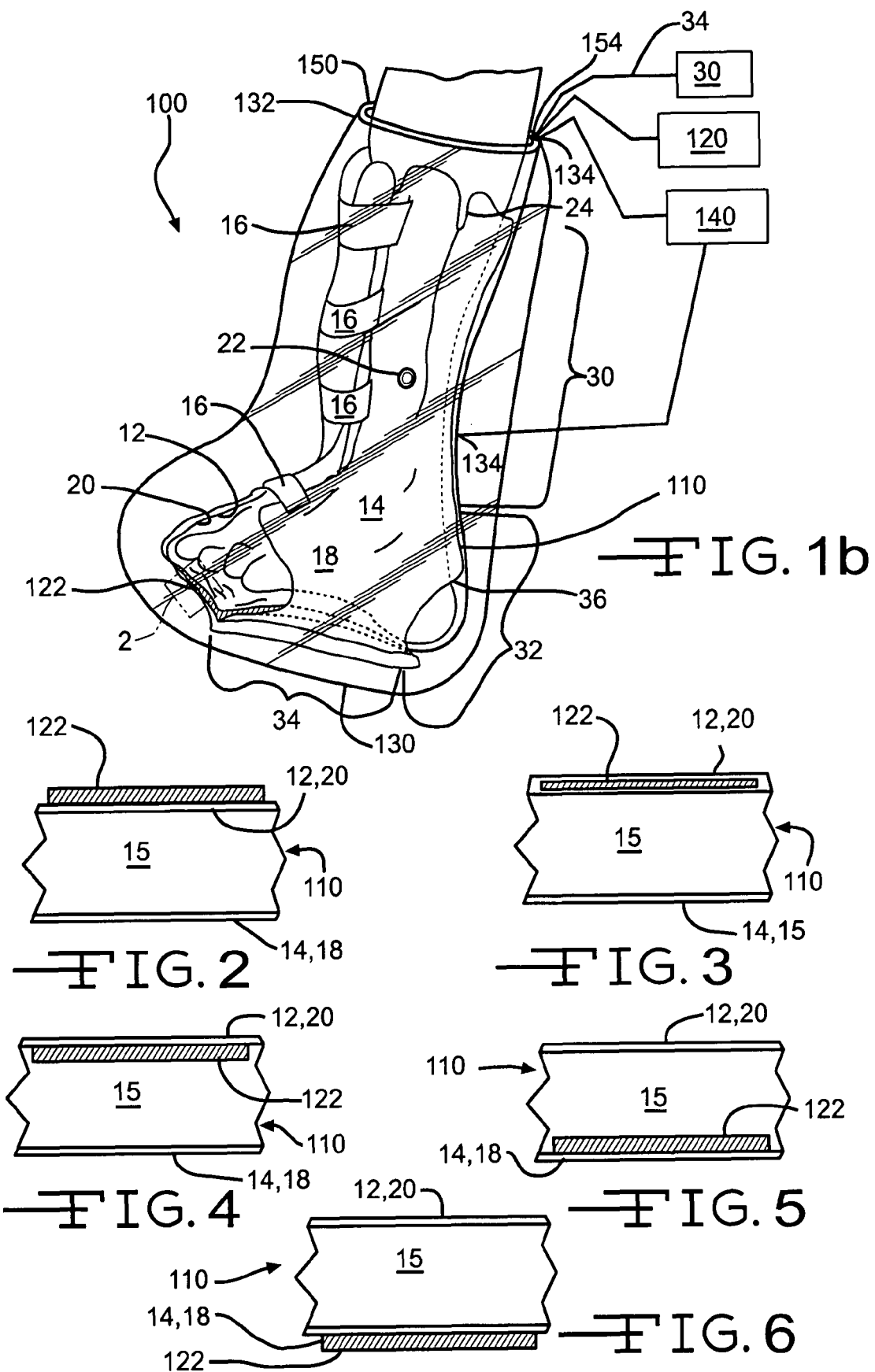

NEGATIVE/POSITIVE PRESSURE, THERMAL ENERGY THERAPY DEVICE

FIELD OF THE INVENTION

The present invention is directed to an alternative embodiment of a negative pressure therapy device.

BACKGROUND OF THE INVENTION

Stanford University is the assignee of U.S. Pat. Nos. 5,683,438; 6,602,277; 6,673,099; 6,656,208; 6,966,922; 7,122,047; and 6,974,442. Every device disclosed in those patents is a negative pressure, thermal energy device and has the following elements: (1) an enclosure having an opening to receive a portion of a patient's body that contains a venous plexus area, (2) a vacuum system that creates a negative pressure in the enclosure, (3) a seal positioned at the enclosure's opening to maintain the negative pressure in the enclosure, and (4) a thermal energy system having a thermal energy contacting element wherein the venous plexus area is supposed to contact the thermal energy contacting element. In addition, these devices are non-disposable products.

Stanford University's Products

A. Enclosure

The enclosure surrounds a portion of a patient's body having a venous plexus area. The venous plexus area is a vascular network formed by numerous anastomoses between veins. A venous plexus area is normally located at the patient's foot area and/or hand area.

The enclosure can be shaped like a glove, a mitten, a boot, a clam-shell, or equivalents thereof so long as there is an opening that can receive the patient's body part having a venous plexus area. The enclosure is also a polymeric material that can withstand the formation of predetermined negative pressure values within its interior; the interior receives the patient's body part having a venous plexus area.

B. Seal

The seal is mounted at the enclosure's opening. The opening also receives the patient's body part having a venous plexus area. The seal establishes (1) a vacuum-tight fit between the body portion and the enclosure or (2) a soft seal fit between the body portion and the enclosure.

The term "vacuum-tight", as interpreted by Dr. Grahn in some of the above-identified Stanford patents and he is one of the inventors of all of the Stanford patents, means a hard seal that does not leak. Dr. Grahn's interpretation conforms with General Electric's January 1966 definition of "a vacuum-tight seal is generally considered to be one which, when tested on a helium-peaked mass spectrometer leak detector, shows a leakage rate of less than $10^{-10}$ cm$^3$s$^{-1}$."

The soft seal allows the negative pressure to leak to the ambient environment through the seal so the seal does not create a tourniquet effect on the mammal. A tourniquet effect is obtained through a hard seal and is undesirable because it terminates the blood flow which is contrary to the intent of Stanford's negative pressure, thermal energy device. Even though the soft seal leaks, the negative pressure in the enclosure is maintained by the vacuum system and the soft seal inhibits an immediate loss of the desired negative pressure in the enclosure.

C. Vacuum System

The vacuum system connects to the enclosure for establishing and, in some embodiments, maintaining a predetermined negative pressure inside the enclosure to cause vasodilation in the body portion surrounded in the enclosure. Negative pressure conditions are a pressure lower than ambient pressure under the particular conditions in which the method is performed. The magnitude of the decrease in pressure from the ambient pressure under the negative pressure conditions is generally at least about 20 mmHg, usually at least about 30 mmHg and more usually at least about 35 mmHg. The magnitude of the decrease may be as great as 85 mmHg or greater, but typically does not exceed about 60 mmHg and usually does not exceed about 50 mmHg. Applying the negative pressure condition to a portion of the body in the enclosure (a) lowers the vasoconstriction temperature and/or (b) increases vasodilation in the body portion that is in the enclosure.

The negative pressure inducing element may be actuated in a number of different ways, including through motor driven aspiration, through a system of valves and pumps which are moved through movement of the mammal in a manner sufficient to create negative pressure in the sealed environment.

D. Thermal Energy Contacting Element

The thermal energy contacting element delivers heated thermal energy and/or cold thermal energy at least to the surface of the body portion in the enclosure. While delivering the desired thermal energy, the vacuum system maintains the predetermined negative pressure in the enclosure. That way the local vasodilation in the body portion promotes absorption and transfer of the thermal energy from the surface of the body portion to the body core of said mammal.

The thermal energy contacting element has been disclosed as (a) "a radiant heat lamp" positioned exterior to the enclosure and provides radiant heat to the exterior surface of the enclosure which warms the interior of the enclosure and thereby provides warm thermal energy to the entire body portion in the enclosure—not just a specific portion of the body portion in the enclosure, and (b) warming or cooling blankets, warm or cool water immersion elements, warming or cooling gas elements, and a curved metal plate or a metal tube positioned in the interior of the enclosure. The latter embodiments can have a fluid (i) circulate within and (ii) not contact the body portion in the desired area—the venous plexus area.

Of these embodiments, the metal plate and tube are considered to be the most effective thermal energy contacting elements because they are easy to manufacture, the thermal energy transfer efficiency to the patient are relatively acceptable and the ease of using the product in actual use.

The fluid temperature can be thermally controlled and delivered to the thermal energy contacting element by Gaymar's Medi-Therm III fluid thermal control dispensing unit.

Grahn et al. does not disclose using positive pressure or equivalent thereof to obtain the desired therapy. As a matter of fact, Grahn et al. teaches away from using positive pressure because positive pressure will not create the desired vasodilation.

It has been determined that continuous and/or extended periods of application of negative pressure on a patient may cause edema. Edema should be avoided when possible.

Reversing Edema

In U.S. Pat. No. 6,488,643, Tumey, et al. wrote, "Among the predominant theories for explaining the effects of compression bandaging, edema reduction and control for the improvement of venous hemodynamic abnormality concomitant prolonged venous hypertension from valvular incompetency or dysfunction stands out. It is thought that the reduction and control of edema improves capillary microcirculation, in turn resulting in the elimination of venous ulcers.... [I]t is important to note that it is universally understood that a proper gradient must be established in order to derive the benefits of compression bandaging. This gradient is generally accepted as being from about 35 to 45 mm Hg at the ankle and reducing to about 15 to 20 mm Hg at just below the knee. Often stated in the literature as a prerequisite to good bandaging technique, the maintenance of graduated compression is critical to effective treatment of ulcers. Failure to initially obtain, and thereafter maintain, the desired sub-bandage pressures is fatal to the treatment regimen . . . . Studies show that mechanically produced compression levels may produce ischaemic not noted at similar compression levels obtained through bandaging. The reductions in leg pulsatile blood flow associated with mechanical prophylaxes often occur at compression levels below that necessary for good bandaging effects. This result, sometimes called cuffing, has resulted in most mechanical prevention prophylaxes being contraindicated for patients exhibiting DVT. Consequently, those of ordinary skill in the art have to date steadfastly avoided mechanical prophylaxes for the treatment of venous stasis and other ulcers or edema of the extremities."

Tumey, et al. clearly teaches using any air pressure device to reverse edema is contraindicated.

SUMMARY OF THE INVENTION

A negative/positive pressure, thermal energy therapy device is described in this application. The present invention uses a conventional negative pressure, thermal energy device and/or an alternative embodiment thereof and adds a significant modification. The modification is that positive pressure, not just ambient pressure, is at least occasionally applied to the patient's body contained in the negative pressure, thermal energy device.

BRIEF DESCRIPTION OF THE FIGURES

FIG. 1b illustrates an embodiment of a disposable negative pressure, thermal energy therapy device that provides intermittent positive pressure instead of negative pressure.

FIG. 2 illustrates an enlarged view of FIG. 1b taken from box 2 that conveys a position of the thermal energy contacting element in the modified heel care boot.

FIGS. 3 to 6 illustrate alternative embodiments relating to the position of the thermal energy contacting element in the modified heel care boot.

DETAILED DESCRIPTION OF THE INVENTION

Figure 1A:
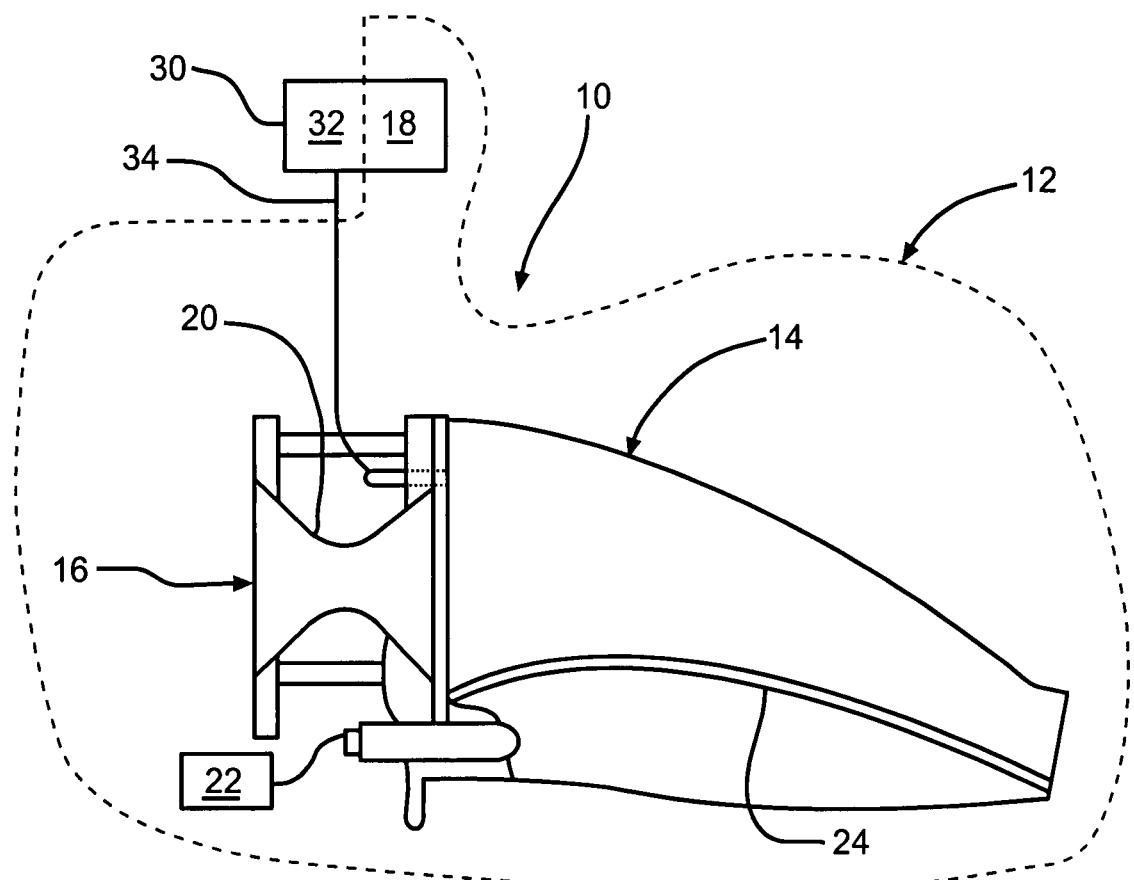
FIG. 1a illustrates a modified conventional negative pressure, thermal energy therapy device that provides intermittent positive pressure instead of negative pressure.

FIG. 1a illustrates a negative/positive pressure, thermal energy therapy device 10 encompassing a patient's foot. The negative/positive pressure, thermal energy therapy device 10 illustrated in FIG. 1a can be divided into two parts. The first part is a conventional negative pressure, thermal energy-therapy device 12. As stated above, the conventional negative pressure, thermal energy therapy device 12 has (1) an enclosure 14 having an opening 16 to receive a portion of a patient's body that contains a venous plexus area, (2) a vacuum system 18 that creates a negative pressure in the enclosure, (3) a seal 20 positioned at the enclosure's opening 16 to retain the pressure in the enclosure 14, and (4) a thermal energy system 22 having a thermal energy contacting element 24 wherein the patient's venous plexus area contacts the thermal energy contacting element. Those components are disclosed in detail in this application's "Background of the Invention." When negative pressure is being applied to the patient's venous plexus area, the conventional negative pressure, thermal energy device operates in the way disclosed in the "Background of the Invention."

The second part of the negative/positive pressure, thermal energy therapy device 10 is the positive pressure system 30 that creates a positive pressure in the enclosure 14. The positive pressure system 30 can be distinct and have a pump 32 that directs positive pressure into the therapy device 10 through a conduit 34. Alternatively, the positive pressure system 30 could be the vacuum system 18 operating in reverse—adding positive pressure, not ambient air, instead generating negative pressure.

Negative pressure in the therapy device 10 is the preferred application to create vasodilation for the effective transfer of thermal energy to or away from the patient. Failing to provide intermittent positive pressure to the patient's venous plexus area and other areas within the enclosure 14, however, can create edema at those areas (and possibly other areas). As such intermittent application of positive pressure to the areas within the enclosure 14 is desired.

The positive pressure can be applied for a second to twenty-four intervals. The positive pressure intervals can occur before, after, in-between, or combinations thereof of applications of negative pressure. The duration of the positive pressure intervals is dependent on the duration of the negative pressure application. The ratio of time in which the positive pressure is applied to the patient in relation to the negative pressure is applied to the patient can be a 1:1 ratio or any alternative duration of time application ratio that promotes the desired vasodilation and decreases the chance of edema. When the positive pressure is hyperbaric pressure the positive pressure is applied before, after, in-between, or combinations thereof of applications of negative pressure; and when the positive pressure is atmospheric pressure the positive pressure is applied in-between the applications of negative pressure. The critical issue is that the positive pressure is applied for a sufficient duration in combination with the negative pressure which causes vasodilation, to decrease the chance of edema and if edema is formed to possibly reverse it.

The positive pressure can be atmospheric pressure or hyperbaric pressure which is greater than atmospheric pressure. In particular, the hyperbaric pressure can range from 0.1 to 45 mm Hg above atmospheric pressure. It is to be understood that when positive pressure is being applied to the patient, negative pressure is not being applied to the patient.
Alternative Embodiment for the Conventional Negative Pressure, Thermal Energy Therapy Device As illustrated in FIG. 1b, a disposable negative pressure, compression, thermal energy therapy device 100 has (1) a modified heel care boot 110 having a thermal energy contacting element 122, (2) a disposable pressure bag 130 that can enclose the modified heel care boot 110 (3) a vacuum system 140 that generates a modulatable negative pressure in the disposable pressure bag 130, (4) a soft seal 150 positioned at the disposable pressure bag's opening to maintain the pressure in the bag 130, and (5) a thermal energy system 120 interconnected to, and/or being, the thermal energy contacting element 122 wherein the patient's venous plexus area of the foot contacts the thermal energy contacting element 122.
Modified Heel Care Boot The modified heel care boot 110 is a variation of a conventional heel care boot. An example of a conventional heel care boot 10 is Gaymar Industries, Inc.'s Sof•Care™ HeelCare™ boot which is pre-inflated to a predetermined pressure. It is known that conventional heel care boots are a protective device intended to receive therein and partially enclose in a cradling fashion a human's foot, heel and calf area. The conventional boot conforms to the contour of the limb to normalize the interface pressure between the conventional boot and the surface of the limb to protect the limb and to maintain a proper blood supply to the soft tissues thereof. In addition, the conventional boot decreases the formation of and facilitates the healing of pressure sores and other types of medical pathologies.

The conventional boot has an interior surface 12 and an exterior surface 14 forming a fluid pressure chamber 15 (shown in FIGS. 2 to 6) and fastening devices 16 for securing the boot 10 about the lower limb. Examples of fastening devices include straps and/or hook-and-loop type fasteners.

The conventional boot can have a pair of sheets, an exterior or outwardly facing sheet 18 and an interior or inwardly facing sheet 20 joined peripherally together forming the single air chamber there between. Interior and exterior sheets 18 and 20 are preferably constructed of plastic material (for example polymeric nonwoven material) and have substantially identical configurations and are adjoined at their peripheries by conventional plastic welding methods.

The conventional boot is divided into (a) an upper portion 30 for engaging and partially enclosing a portion of the calf region of the lower limb, (b) an intermediate portion 32 for engaging and partially enclosing the ankle and Achilles tendon region of the lower limb, and (c) a lower portion 34 for engaging and partially enclosing the foot region of the lower limb.

Intermediate portion 32 can include a cut-out portion 36 integrally formed therein for receiving therein the heel of the foot. Cut-out portion 36 allows for total suspension of the heel thereby creating zero pressure, shear, heat, moisture and bacterial effects on the heel area. This is vitally important because the heel area is a primary area of ulcer formation and treatment, particularly for elderly patients.

The conventional boot can include apertures for preventing bacterial growth, for providing visibility of the body extremity and for providing cooling. Preferably the apertures are located in the conventional boot and formed at the closure. Sheets 18, 20 can, for example, have a plurality of aligned apertures such as holes 22 extending there through with the sheets 18, 20 being joined together by heat sealing means about the circumference of each hole 22 in an airtight fashion. The conventional boot can further include one or more additional ventilation openings such as a slot 24 to provide ventilation to the Achilles region of the limb when the conventional boot is secured thereabout. Openings 22 and 24 act to dissipate heat and/or coolness; and moisture and provide air flow (and pressure) there through, allow palpation of the lower limb for edema (swelling), allows palpation and auscultation of the posterior tibial artery pulse, and provides visibility allowing a care giver to generally view the lower limb there through. By providing ventilation, these openings assist in keeping the lower limb substantially dry and eliminate problems normally associated with the maceration of skin and soft tissue due to continuous high moisture and heat levels, as well as prevent bacterial growth associated with moisture and heat build-up in unventilated areas.

The conventional boot is an inexpensive product to treat pressure sores. For that reason, the conventional boot is conventionally used only in association with a single patient and then disposed. Single patient use is desirable because it decreases the chances of contaminating a patient.

The conventional boot and the modified heel care boot 110 are the same except the modified heel care boot 110 has the thermal energy contacting element 122. The thermal energy contacting element 122 can be positioned (a) on the interior side of the lower portion's 34 interior or inwardly facing sheet 20 (FIG. 2), (b) within the lower portion's 34 interior or inwardly facing sheet 20 (FIG. 3), or (c) on the exterior side of the lower portion's 34 interior or inwardly facing sheet 20 (FIG. 4). That way the thermal energy contacting element 122 provides the desired thermal energy to the patient's a venous plexus area on a foot.

The thermal energy contacting element 122 can be a symmetric conductive design, conductive polymeric material, a convective fitting object positioned near the patient's venous plexus area, conductive beads extending from and interconnected to a conductive plate, warming or cooling blankets like an electric blanket and/or a conductive blanket, warm or cool water immersion elements, warming or cooling gas elements, a curved metal plate or a metal tube. The above-identified thermal energy contacting elements 122 can control the thermal energy by various methods. Some of those methods include a fluid system and/or a resistor system. The fluid system allows a fluid having a predetermined temperature to (i) circulate within the thermal energy contacting element 122 and (ii) not contact the venous plexus area. The fluid can be provided by Gaymar's Medi-Therm delivery and thermal control unit. The resistor system is when an electrical source provides electrical energy to the resistors in the thermal energy contacting element 122 and the resistors generate heated thermal energy of a predetermined temperature.

In another embodiment, the thermal energy contacting element 122 can be positioned (a) on the interior side of the lower portion's 34 exterior facing sheet 18 (FIG. 5) or (b) on the exterior side of the lower portion's 34 exterior facing sheet 18 (FIG. 6). In this embodiment, the thermal energy contacting element 122 can be a light source that radiates heat or a cold source that radiates coldness or any of the other above-identified elements 122. In this embodiment, the thermal energy contacting element 122 is positioned a predetermined distance from the foot's venous plexus area to decrease any radiation damage to the foot. The above-identified thermal energy contacting elements 122 can control the thermal energy by various methods. Some of those methods include a fluid system and/or a resistor system, as described above.

Disposable Pressure Bag

The disposable pressure bag 130 is any material that can (a) surround the modified heel care boot 110 and a portion of the patient's leg and foot; and (b) contain the modulatable negative pressure generated from the vacuum system 140. An example of the material is a polymeric bag having an opening 132 to receive the patient's leg and modified heel care device 110.

The disposable pressure bag 130 may also have an aperture(s) 134 to receive a conduit(s) from the vacuum system 140 and/or the thermal energy system 120.

Soft Seal

The soft seal 150 is positioned at the opening 132 of the disposable pressure bag 130. The soft seal 150 can be an adhesive, an adhesive sheet, a plurality of adhesive sheets, an inflatable fluid bladder that expands and contracts depending on the amount of fluid that enters the bladder, and a polymeric webbing material having a crown shaped foam material positioned between the polymeric webbing material and the patient's body. The soft seal 140 allows some of the pressure to escape and simultaneously allows the pressure to be applied to the patient's leg.

The soft seal 150 may also have an aperture(s) 154 to receive a conduit(s) from the vacuum system 140 and/or the thermal energy system 120.

Vacuum System

The vacuum system 140 differs from the prior negative pressure thermal therapy's vacuum system. One of those differences is that the vacuum system 140 is able to modulate the negative pressure contained within the disposable pressure bag 130. The prior negative pressure, thermal therapy's vacuum system was designed to generate a predetermined negative pressure in the enclosure. The ability to modulate the negative pressure is not new for vacuum systems but it is novel for applications with disposable negative pressure, compression, thermal therapy devices 100.

By modulating the pressure within disposable pressure bag 130, the vacuum system's pressure causes compression therapy to be provided by the modulated heel care boot 110. When the negative pressure within the disposable pressure bag 130 increases the negative pressure contracts the fluid contained within the modulated heel care boot 110. And when the negative pressure within the disposable pressure bag 130 decreases the negative pressure expands the fluid contained within the modulated heel care boot 110. The resulting expansion and contraction of the fluid within the modulated heel care boot 110 causes the desired compression therapy.

Thermal Energy System

The thermal energy system 120 is identical to the prior negative pressure thermal therapy's thermal energy system.

While the present invention has been described and illustrated in conjunction with a number of specific embodiments, those skilled in the art will appreciate that variations and modifications may be made without departing from the principles of the invention as herein illustrated, described and claimed. The present invention may be embodied in other specific forms without departing from its spirit or essential characteristics. The described embodiments are to be considered in all respects as only illustrative, and not restrictive. The scope of the invention is, therefore, indicated by the appended claims, rather than by the foregoing description. All changes which come within the meaning and range of equivalency of the claims are to be embraced within their scope.

We claim:

1. A negative pressure, thermal energy therapy device comprising:
    an enclosure having an opening to receive a portion of a patient's body that contains a venous plexus area;
    a vacuum system that creates a negative pressure in the enclosure, the negative pressure in the enclosure is sufficient to cause the patient's veins to vasodilate;
    a positive pressure system that creates a positive pressure in the enclosure, the positive pressure in the enclosure is sufficient to (i) decrease the chance of a patient having edema, (ii) prevent the patient from having edema, and/or (iii) reverse the patient's edema, when the positive pressure is hyperbaric pressure the positive pressure is applied before, after, in-between, or combinations thereof of applications of negative pressure; and when the positive pressure is atmospheric pressure the positive pressure is applied in-between the applications of negative pressure;
    a seal positioned at the enclosure's opening to retain the pressure in the enclosure;
    a thermal energy system having a thermal energy contacting element wherein the patient's venous plexus area contacts the thermal energy contacting element; and
    an inflatable heel care boot positioned inside of said enclosure and adapted to receive the portion of the patient's body, said inflatable heel care boot including a pressure chamber containing a fluid which does not come into contact with the portion of the patient's body.

2. The device of claim 1 wherein the seal is a soft seal.

3. The device of claim 1 wherein the enclosure receives a fluid and the fluid is air.

4. The device of claim 1 wherein the negative pressure modulates.

5. The device of claim 1 wherein the thermal energy contacting element is selected from the group consisting of a light source that radiates heat, a cold source that radiates coldness, a symmetric conductive design, conductive polymeric material, a convective fitting object positioned near the patient's venous plexus area, conductive beads extending from and interconnected to a conductive plate, warming or cooling blankets like an electric blanket and/or a conductive blanket, warm or cool water immersion elements, warming or cooling gas elements, a curved metal plate or a metal tube.

6. The device of claim 5 wherein the thermal energy transferred from the thermal energy contacting element is through a fluid system.

7. The device of claim 5 wherein the thermal energy transferred from the thermal energy contacting element is through a resistor system.

8. The device of claim 1 wherein the vacuum system and the positive pressure system are the same.

9. A negative pressure, thermal energy therapy device comprising:
    an enclosure having an opening to receive a portion of a patient's body;
    a vacuum system that creates a negative pressure in the enclosure, the negative pressure in the enclosure is sufficient to cause the patient's blood vessels to vasodilate;
    a positive pressure system that creates a hyperbaric positive pressure in the enclosure;
    a seal positioned at the enclosure's opening to retain the pressure in the enclosure;
    a thermal energy system having a thermal energy contacting element that influences the temperature of the portion of the patient's body in the enclosure; and
    an inflatable heel care boot positioned inside of said enclosure and adapted to receive the portion of the patient's body, said inflatable heel care boot including a pressure chamber containing a fluid which does not come into contact with the portion of the patient's body.

10. The device of claim 9 wherein the vacuum system and the positive pressure system are the same.

11. The device of claim 9 wherein the negative pressure modulates.

12. The device of claim 9 wherein the thermal energy is transferred from the thermal energy contacting element to the portion of the patient's body via a fluid.

* * * * *